United States Patent [19]

Grossman

[11] Patent Number: 4,539,846

[45] Date of Patent: Sep. 10, 1985

[54] HIGH RESOLUTION IN SITU ULTRASONIC CORROSION MONITOR

[75] Inventor: Robert J. Grossman, Schenectady, N.Y.

[73] Assignee: The United States of America as represented by the United States Department of Energy, Washington, D.C.

[21] Appl. No.: 569,700

[22] Filed: Jan. 10, 1984

[51] Int. Cl.³ .......................................... G01N 29/04
[52] U.S. Cl. ......................................... 73/579; 73/86; 422/53
[58] Field of Search .................. 73/86, 597, 61.2; 422/53

[56] References Cited

U.S. PATENT DOCUMENTS

| | | | |
|---|---|---|---|
| 2,619,605 | 11/1952 | Lancor | 73/35 X |
| 3,350,942 | 11/1967 | Peltola | 73/597 X |
| 3,540,265 | 11/1970 | Lynnworth | 73/597 X |
| 4,161,665 | 7/1979 | Buck et al. | 73/35 X |
| 4,440,862 | 4/1984 | Cheng et al. | 422/53 X |

Primary Examiner—Anthony V. Ciarlante
Attorney, Agent, or Firm—Judson R. Hightower

[57] ABSTRACT

An ultrasonic corrosion monitor is provided which produces an in situ measurement of the amount of corrosion of a monitoring zone or zones of an elongate probe placed in the corrosive environment. A monitoring zone is preferably formed between the end of the probe and the junction of the zone with a lead-in portion of the probe. Ultrasonic pulses are applied to the probe and a determination made of the time interval between pulses reflected from the end of the probe and the junction referred to, both when the probe is uncorroded and while it is corroding. Corresponding electrical signals are produced and a value for the normalized transit time delay derived from these time interval measurements is used to calculate the amount of corrosion.

15 Claims, 4 Drawing Figures

HIGH RESOLUTION IN SITU ULTRASONIC CORROSION MONITOR

FIELD OF INVENTION

The present invention relates to a high resolution ultrasonic method and apparatus for continuously monitoring corrosion film buildup. The U.S. Government has rights in this invention pursuant to Contract No. EY-76-12-0052 between the U.S. Department of Energy and General Electric Co.

BACKGROUND OF THE INVENTION

As component corrosion becomes an increasingly important consideration in lifetime reliability, it also becomes more important to be able to predict and measure that corrosion. For example, there are strong incentives to increase nuclear fuel element linear heat ratings, coolant temperatures, and/or in-reactor residence times. Consequently, there is a growing need to be able to understand and characterize zircaloy cladding corrosion as well as to monitor corrosion. The traditional approach used to characterize corrosion behavior is to use discrete data obtained by periodically weighing test specimens. This requires non-productive shutdown of the test facility and lost time while the measurement is made. Furthermore, it is virtually impossible to characterize instantaneous corrosion rates with discrete data, particularly through transition regions where rates may change dramatically over short periods of time.

A number of different techniques have been developed in measuring the effects of corrosion. For example, U.S. Pat. No. 3,253,219 (Littler) discloses a method of determining corrosion rate using the change in the output frequency of a piezoelectric crystal to which a corrodible specimen is attached. A further type of corrosion-measuring device is disclosed in U.S. Pat. No. 3,056,284 (Marsh et al) which determines the coating of a foreign material on, or the loss of exposed surface from, a test or reflectance element, and which employs an elongate body having at least two pairs of reflecting surfaces. An ultrasonic wave of a selected frequency is applied to the body and multiple reflections are produced. The applied frequency is adjusted to provide a condition of internally reflected resonance. Further, U.S. Pat. No. 3,104,355 (Holmes et al) discloses a corrosion measuring probe with a temperature compensating element connected in a Wheatstone bridge. Other general measurement techniques of possible interest here include those disclosed in U.S. Pat. No. 2,280,226 (Firestone) which relates to a flaw detecting device in which high frequency vibrations are transmitted into a part to be inspected for flaws and the intervals of direct and reflected vibrations are determined; U.S. Pat. No. 3,004,425 (Henry) which discloses the use of a piezoelectric transducer in combination with ultrasonic pulse echo techniques to provide inspection of a test specimen close to the entrant surface; and U.S. Pat. No. 3,587,299 (Taley) which discloses a char rate detector employing an ultrasonic sound generator and sound wave reflectors embedded at predetermined depths between two opposing surfaces of virgin ablative material.

SUMMARY OF THE INVENTION

In accordance with the invention, an ultrasonic corrosion monitor is provided which produces a continuous, in-situ indication of the corrosion film building up. In general, the monitor is based on the principle that, under certain conditions, the effective longitudinal ultrasonic velocity in a corroding waveguide changes as the corrosion film builds up. The film thickness measurement resolution provided by the ultrasonic corrosion monitor of the invention is a function of the material under test, the specific monitor geometry, and the resolution of the signal processing system, although typical resolutions are better than 0.1 um (0.004 mil). The ultrasonic corrosion monitor of the invention provides a very powerful tool for characterizing and monitoring corrosion. Potential applications include: (1) laboratory studies for basic understanding of the corrosion process; (2) in-situ, continuous measurement of test specimen corrosion under controlled conditions to develop predictive tools or for quality control; and (3) monitoring the corrosion of operating components in an operating plant.

In accordance with a preferred embodiment of the invention an in situ ultrasonic corrosion monitoring system is provided which comprises an elongate corrodible probe including at least one monitoring zone defined between first and second discontinuities, and being adapted to be exposed to a corrosive environment; means for continuously applying ultrasonic pulses to the monitoring zone of the probe while the probe is exposed to the corrosive environment, for receiving the corresponding pulses reflected from the first and second discontinuities, and for converting the received pulses into corresponding electrical signals; and signal processing means for determining the time delay intervals between the electrical signals corresponding to the pulses reflected from the first discontinuity and the electrical signals corresponding to the pulses reflected from the second discontinuity while the probe is exposed to the corrosive environment. The determination of the time delay intervals is used in providing an indication of the corrosion thickness on the monitoring zone of the probe.

In an exemplary embodiment, the first discontinuity is provided at the junction between the monitoring zone and a lead-in portion of the probe and the second discontinuity is provided at the free end of the probe. Further, the pulse receiving means preferably comprises a transducer located at the opposite end of the probe from the monitoring zone. Advantageously, the transducer comprises a magnetostrictive transducer. Preferably, this magnetostrictive transducer comprises a magnetostrictive stub attached to a lead-in portion of the probe and a coil surrounding the stub. Advantageously, an external magnetic field is provided for enhancing the magnetostriction effect of said magnetostrictive transducer. The pulse applying means and reflected pulse receiving means preferably comprises a pulser/receiver to generate electrical pulses to cause ultrasonic pulses to be applied to the probe and by which ultrasonic pulses reflected by the probe are received and converted into corresponding electrical signals. The monitoring system can further include calibration means, including a calibration wire subjected to the same corrosive environment as the probe, for assisting in calibrating the time delay interval measurements.

In accordance with a further aspect of the invention, an in situ corrosion monitoring method is provided which comprises locating, in a corrosive environment, a corrodible monitoring probe having at least one monitoring zone defined between first and second discontinuities; applying ultrasonic pulses to the monitoring zone of the probe; detecting the ultrasonic pulses reflected from the first and second discontinuities; determining the time interval between the reflected pulses; and using the time interval determination to determine the amount of corrosion of the probe. Preferably, these time interval determinations are made initially on the monitoring zone of the uncorroded probe and subsequently on the monitoring zone as the probe corrodes. The ratio of the corroded to uncorroded time interval measurements is referred to as the normalized delay time. This ratio is set equal to $$\left[\frac{1 + F_1F_2F_3}{1 + F_2F_3}\right]^{-\frac{1}{2}}$$

where $F_1$ is equal to the square of the ratio of the ultrasonic velocity in the corrosion film divided by the ultrasonic velocity in the base metal; $F_2$ is equal to the corrosion film density divided by the base metal density; and $F_3$ is the corrosion film cross-sectional area divided by the base metal cross-sectional area. Another aspect of the method of the invention involves calibrating the probe using a calibration wire exposed to the same corrosive environment, the calibration wire being removed from the corrosive environment to determine the amount of corrosion thereof. Temperature measurements are made within the corrosive environment to adjust the measured time intervals to a fixed temperature because temperature changes also cause ultrasonic velocity changes in the monitoring zone of the probe.

Other features and advantages of the invention will be set forth in, or apparent from, the detailed description of the preferred embodiments which follows.

DESCRIPTION OF THE PREFERRED EMBODIMENTS

Figure 1:
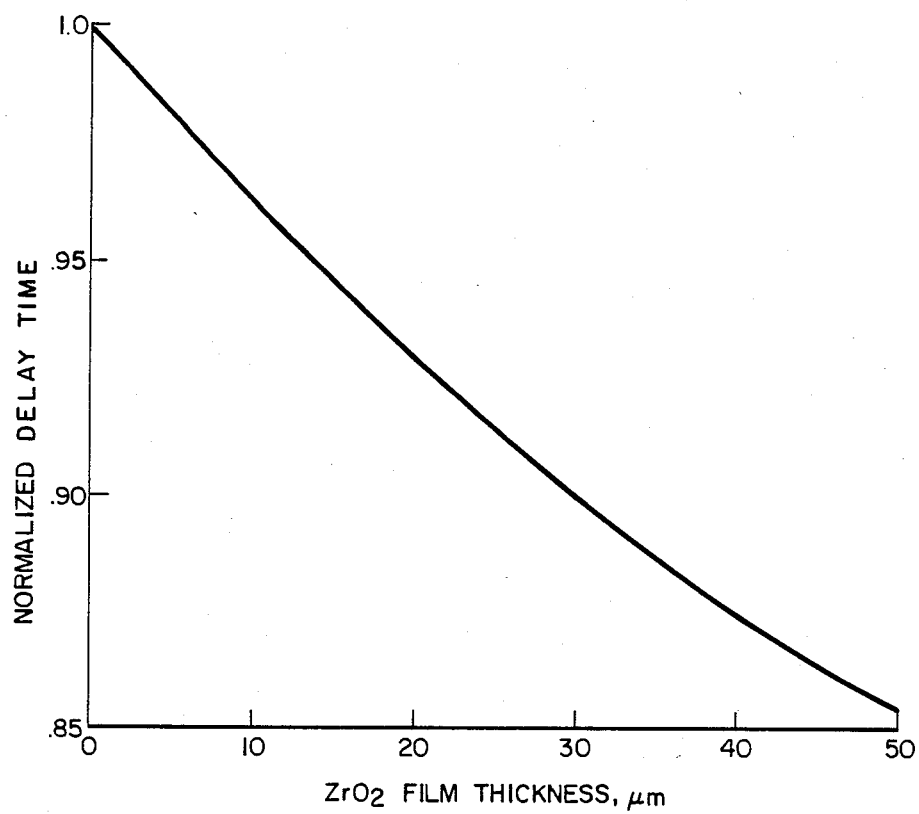
FIG. 1 is a graph of the predicted dependence of the normalized delay time on corrosion film thickness, for a 0.76-mm diameter zircaloy ultrasonic corrosion monitor.

Turning first to the model on which the present invention is based, the extensional ultrasonic velocity, V, along the axis of a thin metal wire is given by the formula:

$$V = \sqrt{E/\rho} \qquad (1)$$

where E is Young's Modulus and $\rho$ is the density. This equation is valid for wavelengths greater than about 10 times the wire diameter. In a corroding environment, an annulus of corrosion product replaces the outer rim of the wire. It has been shown that the wave propagation characteristics of such a composite cross-section are similar to those in a homogeneous wire having properties approximating the weighted average of the base metal and the corrosion film. The effective longitudinal velocity, $V_E$, thus becomes:

$$V_E = V_M \left[\frac{1 + F_1F_2F_3}{1 + F_2F_3}\right]^{\frac{1}{2}} \qquad (2)$$

where $V_M$ = ultrasonic velocity in base metal;

$$F_1 = \left[\frac{V_c}{V_M}\right]^2 = \left[\frac{\text{ultrasonic velocity in corrosion product}}{\text{ultrasonic velocity in base metal}}\right]^2;$$

$$F_2 = \frac{\rho_c}{\rho_M} = \frac{\text{density of corrosion product}}{\text{density of base metal}};$$

$$F_3 = \frac{A_c}{A_M} = \frac{\text{corrosion film cross-sectional area}}{\text{base metal cross-sectional area}};$$

$A_M$ and $A_c$ are functions of the initial probe radius, r; and the ratio $$F_4 = \frac{t_M}{t_c} = \frac{\text{metal thickness lost}}{\text{corrosion thickness gained}}.$$

Thus, $$F_3 = \frac{t_c}{r - F_4 t_c}\left[2 + \frac{t_c}{r - F_4 t_c}\right] \qquad (3)$$

and the effective longitudinal velocity will change with increasing corrosion film thickness, as long as $V_M \neq V_c$.

The travel time, $\Delta t$, of the ultrasonic wave through a wire length L is given by the formula $$\Delta t = L/V_E \qquad (4)$$

The normalized delay time is the ratio of the travel time in the corroded wire, $\Delta t_{corr}$, to that in the same length of initially uncorroded wire, $\Delta t_{bare}$ and thus may be represented as follows:

$$\frac{\Delta t_{corr}}{\Delta t_{bare}} = \frac{V_{bare}}{V_{corr}} \qquad (5)$$

$$= \frac{V_M}{V_E}$$

$$= \left[\frac{1 + F_1F_2F_3}{1 + F_2F_3}\right]^{-\frac{1}{2}}$$

It is expected that this expression can be applied to waveguides of arbitrary cross-sectional geometry by appropriately modifying the $F_3$ term.

The normalized delay time can be determined for any corrosion film thickness, $t_c$, from Equations (3) and (5). For example, consider a 0.76-mm diameter (0.030 inch) zircaloy wire in an oxidizing environment. For zircaloy/$ZrO_2$ in the range of 500° to 1000° F., $F_1 = 2.8$, $F_2 = 0.85$, and $F_4 = 0.67$. The predicted normalized delay time as a function of corrosion film thickness for the example under consideration is shown in FIG. 1.

The predicted resolution of the ultrasonic corrosion monitor of the invention is a function of: (1) the probe radius (the resolution increases as radius decreases); (2)

the probe length (the resolution increases as length increases); (3) the probe material (as this material affects $F_1$, $F_2$, and $F_4$); and (4) the signal processing system measurement resolution. The minimum measurable change in corrosion film thickness can be predicted by finding the slope of the curve in FIG. 1 and dividing into the minimum measurable change in delay time. It is noted that there is a weak sensitivity to the instantaneous film thickness such that the resolution decreases slightly as the film thickness increases.

The signal processing system that has been used has a minimum measurable change in delay time of 5 nsec ($5 \times 10^{-9}$ seconds). Thus, for the zircaloy/$ZrO_2$ example discussed above, a minimum measurable change in corrosion film thickness of <0.06 μm (<0.0024 mil) is provided for a 0.76-mm (0.030 inch) diameter, 7-cm long probe. This extremely fine resolution can be even further improved by making the probe longer and/or decreasing the diameter.

Figure 2:
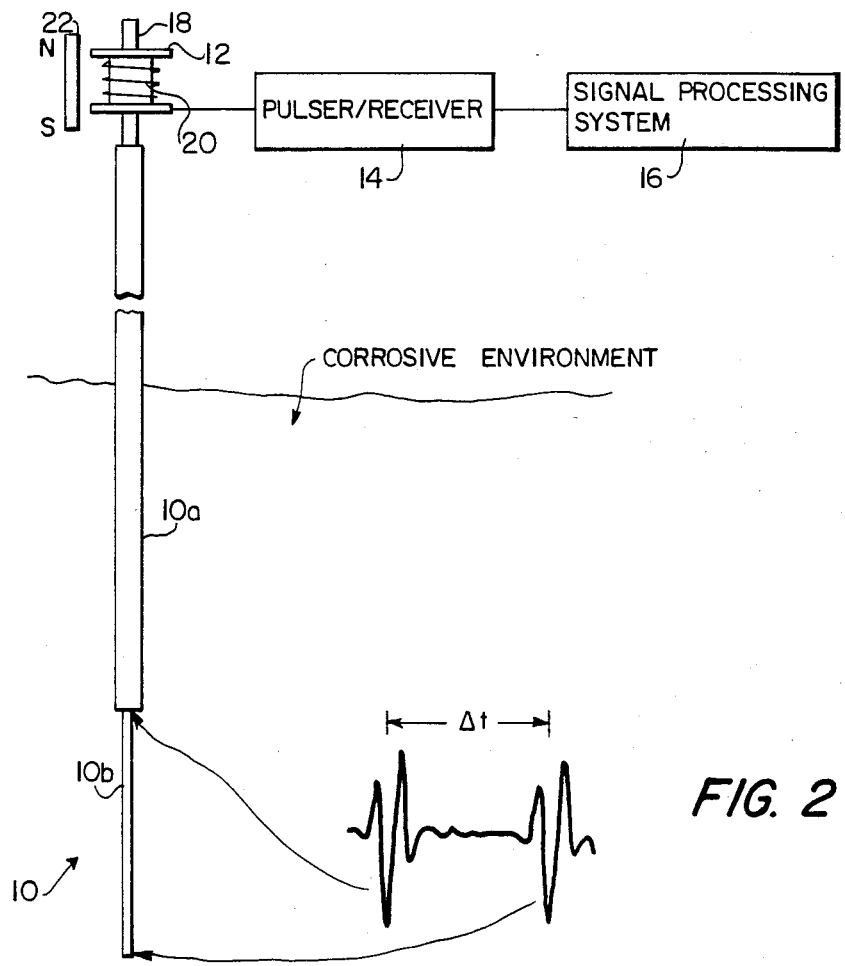
FIG. 2 is a schematic diagram, partly in block form, of an ultrasonic corrosion monitor constructed in accordance with a preferred embodiment of the invention.

Referring to FIG. 2, the principal components of the ultrasonic corrosion monitor of the invention are shown schematically. These components comprise a thin wire probe, denoted 10, which may include a lead-in section 10a and one (or more) sensor zones 10b, a magnetostrictive transducer, generally denoted 12, a pulser/receiver 14 and a signal processing system 16. The magnetorestrictive transducer 12 comprises a magnetostrictive stub 18 which is attached to one end of the lead-in section 10a and surrounded by a pulsing receiving coil 20. An external magnetic field, represented schematically by magnet 22, is applied to enhance the magnetostriction effect. The wire sensor zones referred to above are defined by acoustic impedance discontinuities such as notches or diameter changes. Thus, a first zone is defined between the end of probe 10 and the junction between the reduced diameter portion of the wire probe defining zone 10b and the lead-in portion 10a. As stated, a series of such zones can be provided.

In operation, when an injected pulse encounters the first impedance discontinuity, which, in the example under consideration is the junction between lead-in 10a and reduced diameter portion 10b, it is partially reflected and returns to the transducer to mark the beginning of a time interval. The remainder of the pulse travels on to the next discontinuity, which, in this example, is the end of the wire probe 10, where the next reflection occurs. This marks the end of the first time interval as well as the beginning of a second time interval if there is more than one sensor zone. The corresponding pulses are indicated at the bottom of FIG. 2 along with the time interval Δt. The reflected ultrasonic pulses are converted to electrical pulses by the transducer 12 and sent through the receiver 14 to the signal processing system 16 where the time interval measurement is performed. This time interval between the two pulses is used to determine the average corrosion film thickness on the sensor zone of the probe.

Figure 3:
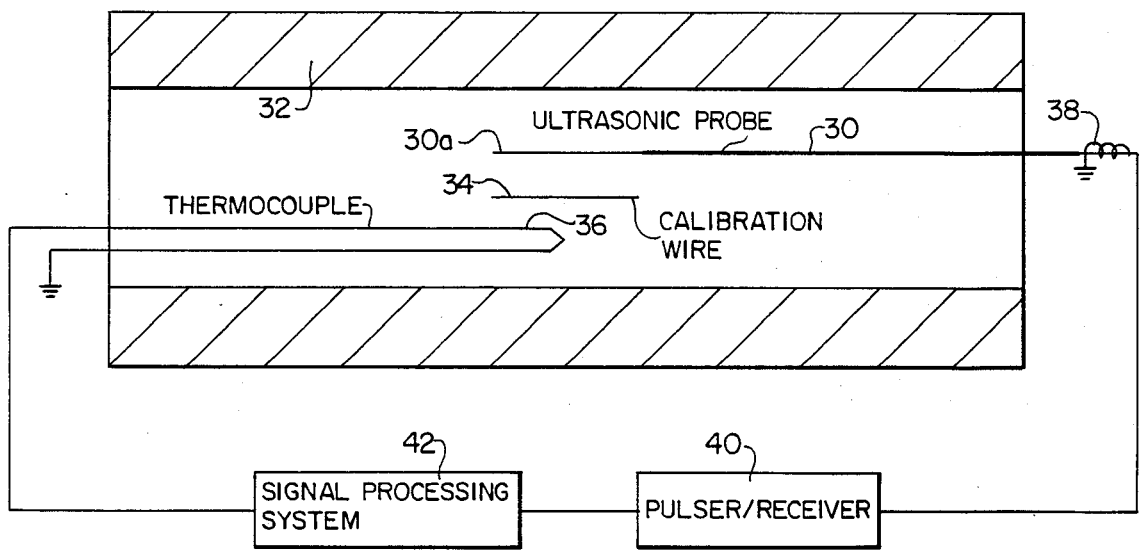
FIG. 3 is a schematic diagram, partly in block form, of an experimental set-up used in demonstration of the operability of, and in providing calibration of, the ultrasonic probe of the invention.

Referring to FIG. 3, a schematic showing is provided of test apparatus used in a "proof-of-principle" experiment. In this experiment, a zircaloy ultrasonic probe, denoted 30, was corroded in an air furnace 32 and the ultrasonic pulse delay time through the probe sensor zone 30a was continuously measured. A second zircaloy wire 34 was corroded beside the ultrasonic probe 30 to serve as a calibration wire. The calibration wire was periodically removed from the furnace 32, weighed, and returned to the furnace to calibrate the change in delay time of the probe 30 to the weight gain of the calibration wire 34.

Considering a specific example, the ultrasonic probe 30 used was a 21-cm long alpha-annealed zircaloy wire with a lead-in diameter of 0.152 cm. The sensor zone 30a was formed by chemically etching a 7-cm length to a diameter of 0.076 cm. The zircaloy calibration wire 34 had the same length and diameter as the sensor zone 30a of the probe 30. Type K (Chromel-Alumel) thermocouples, indicated schematically at 36, were used to measure the furnace temperature and provide input to the furnace controller. The probe 30 is coupled to a transducer 38 which is connected through a pulser/receiver 40 to a signal processing system 42 in the manner described above in connection with FIG. 2. The signal processing system 42 is a Tektronix WP3201 system which includes a 200 MHz, Tektronix 7612D programmable waveform digitizer. This system is capable of making ultrasonic pulse echo delay time measurements with 5 nanosecond resolution, independent of the absolute delay time between pulses. The pulser/receiver 40 used to generate and receive the transducer signal is a Panametrics 5055 PRM. In a specific experiment, the total exposure time of the probe 30 and calibration wire 34 was 1000 hours. The first 381.2 hours were at approximately 850° F. except for a 25-hour period at about 875° F. The temperature was then increased to about 950° F. for the remainder of the experiment to increase the corrosion rate. The temperature was held to about a 5° F. range over long time periods. After 381.2 hours at 850° F. (except for 25 hours at 875° F. ) the weight gain of the calibration wire was 256.5 mg/$dm^2$, which corresponds to a corrosion film thickness of 17.4 μm (0.68 mil) assuming 1 mg/$dm^2$=0.06767 μm=0.00267 mil for zircaloy. At this point there was an obvious increase in the corrosion rate due to the temperature increase to 950° F. The total weight gain of the calibration wire 34 at the end of the experiment was 1652 mg/$dm^2$, which corresponds to a film thickness of 111.8 μm (about 4.41 mils). The weight gain history of the ultrasonic probe sensor zone 30a was assumed to be identical to that for the calibration wire 34. The precision of the weight gain data can be inferred from the calibration wire measurements made at the end of the 850° F. heating period and three hours later after the 950° F. operation had equilibrated. The difference in the two data points is about 4 mg/$dm^2$.

Turning now to the ultrasonic probe results, measurements were made of the round trip travel time, Δt, of the ultrasonic pulse through the sensor zone 30a (i.e., back and forth through the 7-cm section) as a function of the exposure time. The data were collected at the rate of two delay time measurements per minute which is far more than necessary for most applications. A step increase was produced in Δt at about 300 hours due to a 25° F. excursion since the ultrasonic velocity decreases with increasing temperature. This was further illustrated after the temperature increase to 950° F. to accelerate the experiment.

Up to about 600 hours of exposure, corrosion of the ultrasonic probe 30 causes a continual decrease in Δt, which is in agreement with the model and prediction shown in FIG. 1. At 600 hours the weight gain is approximately 800 mg/$dm^2$, which corresponds to a corrosion film thickness of 54.1 μm (2.1 mil). After 600 hours, the rate of change of Δt with exposure time decreases to the point of reaching a minimum at about 675 hours and then actually reverses its slope. This behavior implies a dramatic change in the corrosion film and its impact on the effective ultrasonic velocity. Initially, the corrosion film is a dense, tenacious annulus about the base metal core. The ultrasonic velocity in the corrosion film is about 5/3 times that in the base metal. Consequently, as the film begins to form, the effective ultrasonic velocity increases according to Equation (2) set forth above. However, if the film becomes porous or begins to crack it will lose its original ultrasonic transmission characteristics and the effective velocity will begin to return to the base metal value. That this took place was confirmed by transverse and surface photographs of the probe sensor zone 30a at the end of the experiment wherein a distinct, regular pattern of radial, circumferential, and axial cracks was observed. The cracks occur because the volume of the oxide formed is greater than that of the metal consumed. As fresh corrosion product is formed, previously generated oxide is forced outward. Because of the circular geometry, the oxide volume required to maintain a fully dense annulus is greater than that available. With increasing film thickness the tensile stresses become sufficiently large to fracture the brittle oxide and form crack patterns. In principle, this change in corrosion film properties could be factored into the corrosion monitor data interpretation by adjusting the $F_1$ and $F_2$ factors. It was found that the ultrasonic probe corrosion film thickness at the end of the experiment agreed reasonably well with the measured weight gain of the calibration wire. The film thickness was somewhat variable, tending to follow local grain boundaries at the corroding surface. The average film thickness was about 4.1 mils, compared to the inferred end-of-experiment thickness of 4.41 mils.

The small variations in ultrasonic velocity due to the small temperature variations discussed above, can be normalized to constant 850° F. for the first 381.2 hours and to 950° F. for the remainder of the experiment. The correction was 9 nanoseconds per °F. for the probe under consideration. Although the correction is quite small, it does reveal fine detail which may be obscured by the small temperature variations. Such temperature-normalized ultrasonic probe data can be used to estimate the averge resolution of the ultrasonic probe in this experiment. After 381.2 hours the change in ultrasonic delay time was 2 microseconds or 2000 nanoseconds. The weight gain at this point was 256.5 mg/dm$^2$, corresponding to a film thickness of 17.4 μm. Since the resolution of the signal processing system is 5 nanoseconds, an average minimum measurable change in corrosion film thickness for this probe is given by the relationship:

$$\text{Resolution, } \mu m = \frac{5 \text{ nsec}}{2000 \text{ nsec}/17.4 \text{ }\mu m}$$

$$= 0.0435 \text{ }\mu m \text{ (0.0017 mil)}$$

This is in excellent agreement with a predicted resolution range of 0.03 to 0.06 μm, depending on the film thickness. This is an extremely fine resolution which could be quite useful in developing a detailed understanding of the corrosion process.

Figure 4:
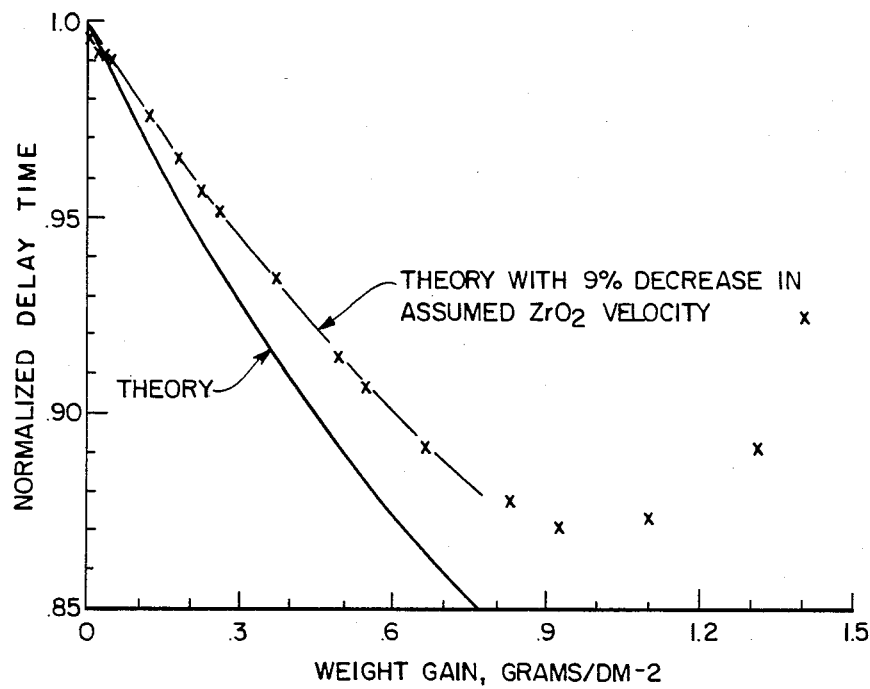
FIG. 4 is a graph comparing the corrosion weight gains inferred from the ultrasonic probe experimental data with the calibration wire weight gains.

Referring to FIG. 4, the ultrasonic probe weight gain, inferred from the calibration wire, has been correlated with the corresponding normalized delay time. According to Equation (5) set forth above, a direct comparison to the model prediction of FIG. 1 can be made. Recognizing that there is considerable uncertainty in the high temperature ultrasonic velocity in ZrO$_2$, the agreement between the theory and the experimental data is excellent. In fact, a decrease of only 9% in the assumed velocity in ZrO$_2$ would put the predicted response right on the data out to 800 to 900 mg/dm$^2$. Naturally, as the corrosion film begins to deteriorate, the data depart from the predicted probe response.

As set forth above, the unique capabilities of the ultrasonic corrosion monitor of the invention enables the monitor to be used in a number of applications. First, the monitor is useful in laboratory studies of the corrosion process. In this regard, the continuous, high resoution data acquired with the ultrasonic probe under controlled laboratory conditions may be used to (1) reveal behavior which contributes to a basic understanding of the corrosion process, and (2) evaluate sensitivities to temperature, corroding medium, and metallurigical variables. For example, this technique can be used to determine instantaneous corrosion rate versus weight gain in a given environment. Further, the monitor can be used in connection with in-situ test specimens. More specifically, such an ultrasonic probe can be used to acquire continuous, long term corrosion data to complement corrosion specimen weight gain data. This could include autoclave environments and, in the case of nuclear materials, test reactor environments. In addition, the invention can be employed as an operating component corrosion monitor. For example, the corrosion of an ultrasonic probe placed in an operating system can be used to infer the corrosion of adjacent components, although this would require a more rugged probe than the simple laboratory probe described above.

The experimental results described above confirm the theoretical model for the ultrasonic corrosion monitor of the invention and confirm the capability thereof in providing a continuous, high resolution indication of corrosion film buildup. Although the ultrasonic probe used in the testing discussed above was cylindrical in shape, further testing was performed with a retangular probe with very similar results. In the more sophisticated form thereof, the ultrasonic corrosion monitor of the invention requires calibration to determine absolute weight gain. However, the monitor can be used without calibration to determine relative corrosion rates, e.g., between materials or as a function of temperature, and to identify consistent structural effects indicated by slope changes.

Although the invention has been described in detail with respect to exemplary embodiments thereof, it will be understood by those of ordinary skill in the art that variations and modifications in these exemplary embodiments may be effected within the scope and spirit of the invention.

I claim:

1. An in situ ultrasonic corrosion monitoring system comprising:
an elongate corrodible probe including at least one monitoring zone defined between first and second discontinuities, and being adapted to be exposed to a corrosive environment;
means for applying ultrasonic pulses to said monitoring zone of said probe while the probe is exposed to the corrosive environment, for receiving the corresponding pulses reflected from said first and second discontinuities, and for converting the received pulses into corresponding electrical signals; and signal processing means for determining the time delay intervals between the electrical signals corresponding to the pulses reflected from the first discontinuity and the electrical signals corresponding to pulses reflected from the second discontinuity while the probe is exposed to the corrosive environment, and for providing an indication of the corrosion thickness on the monitoring zone of said probe based on said determination of the time delay intervals.

2. An in situ ultrasonic corrosion monitoring system as claimed in claim 1 wherein said first discontinuity is provided at the junction between said monitoring zone and a lead-in portion of said probe and said second discontinuity is provided at the free end of the probe.

3. An in situ ultrasonic corrosion monitoring system as claimed in claim 1 wherein said pulse generating and receiving means comprises a transducer located at the opposite end of said probe from said monitoring zone.

4. An in situ ultrasonic corrosion monitoring system as claimed in claim 3 wherein said transducer comprises a magnetostrictive transducer.

5. An in situ ultrasonic corrosion monitoring system as claimed in claim 4 wherein said magnetostrictive transducer comprises a magnetostrictive stub attached to a lead-in portion of said probe and a coil surrounding said stub.

6. An in situ ultrasonic corrosion monitoring system as claimed in claim 4 further comprising means for providing an external magnetic field for enhancing the magnetostriction effect of said magnetostrictive transducer.

7. An in situ ultrasonic corrosion monitoring system as claimed in claim 5 wherein said transducer coil comprises a pulsing-receiving coil to which are applied both electrical pulses for pulsing said probe and ultrasonic pulses reflected from said probe.

8. An in situ ultrasonic corrosion monitoring system as claimed in claim 1 wherein said pulse applying means and reflected pulse receiving means comprises a pulser/receiver transducer to which electrical pulses are applied to cause ultrasonic pulses to be applied to the probe and by which ultrasonic pulses reflected by said probe are received and converted into corresponding electrical signals.

9. An in situ ultrasonic corrosion monitoring system as claimed in claim 1 wherein said monitoring system further includes calibration means, including a calibration wire subjected to the same corrosive environment as the probe, for assisting in calibrating the operation of the system.

10. An apparatus as claimed in claim 1 wherein said probe comprises a thin wire and said transducer comprises a magnetostrictive transducer.

11. An in situ corrosion monitoring method comprising:

locating, in a corrosive environment, a corrodible monitoring probe having at least one monitoring zone defined between first and second discontinuities;

applying ultrasonic pulses to the monitoring zone of the said probe;

detecting the ultrasonic pulses reflected from said first and second discontinuities;

determining the time interval between the reflected pulses; and using the time interval determination to determine the amount of corrosion of said probe.

12. A method as claimed in claim 11 wherein said time interval determinations are made as the monitoring zone of the probe is corroding and a ratio of these measurements to the time interval of the uncorroded monitoring zone is obtained corresponding to the normalized delay time delay interval.

13. A method as claimed in claim 12 wherein said ratio is set equal to $$\left[ \frac{1 + F_1 F_2 F_3}{1 + F_2 F_3} \right]^{-\frac{1}{2}}$$

where $F_1$ is equal to the square of the ultrasonic velocity in the corrosion film divided by the ultrasonic velocity in the base metal; $F_2$ is equal to the corrosion film density divided by the base metal density; and $F_3$ is the corrosion film cross-sectional area divided by the base metal cross-sectional area.

14. A method as claimed in claim 11 further comprising calibrating the probe using a calibration wire exposed to the same corrosive environment, said calibration wire being removed from the corrosive environment to determine the amount of corrosion thereof.

15. A method as claimed in claim 11 wherein temperature measurements are made within the corrosive environment and used to adjust the measured time intervals to a fixed temperature.

* * * * *